(12) United States Patent
Vardi et al.

(10) Patent No.: US 6,692,483 B2
(45) Date of Patent: *Feb. 17, 2004

(54) CATHETER WITH ATTACHED FLEXIBLE SIDE SHEATH

(75) Inventors: Gil M. Vardi, Chesterfield, MO (US); Charles J. Davidson, Winnetka, IL (US); Eric Williams, Fairfield, CA (US)

(73) Assignee: Advanced Stent Technologies, Inc., Pleasanton, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/455,299

(22) Filed: Dec. 6, 1999

(65) Prior Publication Data

US 2003/0028233 A1 Feb. 6, 2003

Related U.S. Application Data

(63) Continuation-in-part of application No. 09/325,996, filed on Jun. 4, 1999, now abandoned, which is a continuation-in-part of application No. PCT/US99/00835, filed on Jan. 13, 1999, which is a continuation of application No. 09/007,265, filed on Jan. 14, 1998, now Pat. No. 6,210,429, which is a continuation-in-part of application No. 08/744,002, filed on Nov. 4, 1996, now abandoned.

(60) Provisional application No. 60/088,301, filed on Jun. 5, 1998.

(51) Int. Cl.[7] .............................................. A61M 25/098
(52) U.S. Cl. ....................... 604/529; 604/284; 623/1.11; 606/108
(58) Field of Search ............................ 623/1.11, 1.35, 623/1.21, 1.23, 1.16, 1.15, 1.14; 606/153, 191, 194, 108, 192, 195, 198; 604/508, 96.01, 103.1, 171, 264, 523, 528–529, 284

(56) References Cited

U.S. PATENT DOCUMENTS 1,596,754 A    8/1926  Moschelle
3,872,893 A    3/1975  Roberts
4,140,126 A    2/1979  Choudhury (List continued on next page.)

FOREIGN PATENT DOCUMENTS

DE        29701758    7/1997
EP          804907    5/1997

(List continued on next page.)

OTHER PUBLICATIONS

Caputo et al., "Stent Jail: A Minimum–Security Prison": *The American Journal of Cardiology*, (1996) 7:1226–1230.

(List continued on next page.)

Primary Examiner—David J. Isabella
Assistant Examiner—Urmi Chattopadhyay
(74) Attorney, Agent, or Firm—Patton Boggs LLP (57) ABSTRACT

A method of positioning a main stent at a vessel bifurcation such that a side opening in the main stent is positioned at the ostium of a branch vessel, comprising: positioning a main guidewire in the main vessel such that a distal end of the main guidewire extends past the bifurcation; advancing a stent delivery system to a position proximate the bifurcation, the stent delivery system comprising a catheter with a flexible side sheath attached thereto, wherein the catheter is received over the main guidewire, and wherein the main stent is positioned over the catheter with the flexible side sheath positioned to pass through the interior of the main stent and out of the side opening in the main stent; advancing a branch guidewire through the flexible side sheath attached to the catheter and into the branch vessel; and subsequently, advancing the catheter over the main guidewire while advancing the flexible side sheath over the branch guidewire while viewing relative movement of a marker positioned on the flexible side sheath with respect to at least one marker positioned on the catheter, wherein the relative movement indicates that a portion of the flexible side sheath adjacent the side opening in the main stent is advancing into the ostium of the branch vessel, thereby indicating the position of the side opening of the main stent with respect to the ostium of the branch vessel.

24 Claims, 13 Drawing Sheets

U.S. PATENT DOCUMENTS

| | | |
|---|---|---|
| 4,410,476 A | 10/1983 | Redding et al. |
| 4,413,989 A | 11/1983 | Schjeldahl et al. |
| 4,421,810 A | 12/1983 | Rasmussen |
| 4,503,569 A | 3/1985 | Dotter |
| 4,552,554 A | 11/1985 | Gould et al. |
| 4,681,570 A | 7/1987 | Dalton |
| 4,689,174 A | 8/1987 | Lupke |
| 4,733,665 A | 3/1988 | Palmaz |
| 4,739,762 A | 4/1988 | Palmaz |
| 4,762,128 A | 8/1988 | Rosenbluth ................ 128/343 |
| 4,769,029 A | 9/1988 | Patel |
| 4,872,874 A | 10/1989 | Taheri |
| 4,900,314 A | 2/1990 | Quackenbush |
| 4,957,501 A | 9/1990 | Lahille et al. |
| 4,957,508 A | 9/1990 | Kaneko et al. |
| 4,994,071 A | 2/1991 | MacGregor |
| 5,042,976 A | 8/1991 | Ishitsu et al. |
| 5,054,501 A | 10/1991 | Chuttani et al. |
| 5,061,240 A | 10/1991 | Cherian |
| 5,064,435 A | 11/1991 | Porter |
| 5,102,403 A | 4/1992 | Alt |
| 5,104,404 A | 4/1992 | Wolff |
| 5,122,125 A | 6/1992 | Deuss |
| 5,147,317 A | 9/1992 | Shank et al. |
| 5,217,440 A | 6/1993 | Frassica |
| 5,254,619 A | 10/1993 | Ando |
| 5,304,220 A | 4/1994 | Maginot |
| 5,337,733 A | 8/1994 | Bauerfeind et al. |
| 5,387,235 A | 2/1995 | Chuter |
| 5,404,887 A | 4/1995 | Prather |
| 5,409,458 A | 4/1995 | Khairkhahan et al. |
| 5,413,586 A | 5/1995 | Dibie et al. |
| 5,417,208 A | 5/1995 | Winkler |
| 5,443,497 A | 8/1995 | Venbrux |
| 5,445,624 A | 8/1995 | Jimenez |
| 5,449,373 A | 9/1995 | Pinchasik et al. |
| 5,456,712 A | 10/1995 | Maginot |
| 5,458,605 A | 10/1995 | Klemm |
| 5,489,271 A | 2/1996 | Andersen |
| 5,489,295 A | 2/1996 | Piplani et al. |
| 5,496,292 A | 3/1996 | Burnham |
| 5,507,769 A | 4/1996 | Marin et al. |
| 5,522,801 A | 6/1996 | Wang |
| 5,531,788 A | 7/1996 | Dibie et al. |
| 5,545,132 A | 8/1996 | Fagan et al. |
| 5,562,724 A | 10/1996 | Vorwerk et al. |
| 5,562,725 A | 10/1996 | Schmitt et al. |
| 5,575,818 A | 11/1996 | Pinchuk |
| 5,593,442 A | 1/1997 | Klein |
| 5,607,444 A | 3/1997 | Lam |
| 5,613,980 A | 3/1997 | Chauhan |
| 5,613,981 A | 3/1997 | Boyle et al. |
| 5,617,878 A | 4/1997 | Taheri |
| 5,628,788 A | 5/1997 | Pinchuk |
| 5,632,763 A | 5/1997 | Glastra |
| 5,634,902 A | 6/1997 | Johnson et al. |
| 5,639,278 A | 6/1997 | Dereume et al. |
| 5,643,340 A | 7/1997 | Nunokawa |
| 5,653,743 A | 8/1997 | Martin |
| 5,669,924 A | 9/1997 | Shaknovich |
| 5,669,932 A | 9/1997 | Fischell et al. |
| 5,676,696 A | 10/1997 | Marcade |
| 5,676,697 A | 10/1997 | McDonald |
| 5,693,084 A | 12/1997 | Chuter |
| 5,693,086 A | 12/1997 | Goicoechea et al. |
| 5,707,354 A | 1/1998 | Salmon et al. |
| 5,709,713 A | 1/1998 | Evans et al. |
| 5,716,365 A | 2/1998 | Goicoechea et al. |
| 5,718,724 A | 2/1998 | Goicoechea et al. |
| 5,720,735 A | 2/1998 | Dorros |
| 5,723,004 A | 3/1998 | Dereume et al. |
| 5,733,303 A | 3/1998 | Israel et al. |
| 5,749,825 A | 5/1998 | Fischell et al. |
| 5,755,734 A | 5/1998 | Richter et al. |
| 5,755,735 A | 5/1998 | Richter et al. |
| 5,755,770 A | 5/1998 | Ravenscroft |
| 5,755,778 A | 5/1998 | Kleshinski |
| 5,762,631 A | 6/1998 | Klein |
| 5,800,508 A | 9/1998 | Goicoechea et al. |
| 5,824,036 A | 10/1998 | Lauterjung |
| 5,824,040 A | 10/1998 | Cox et al. |
| 5,824,044 A | 10/1998 | Quiachon et al. |
| 5,827,320 A | 10/1998 | Richter et al. |
| 5,836,966 A | 11/1998 | St. Germain |
| 5,851,210 A | 12/1998 | Torossian ................ 606/108 |
| 5,851,464 A | 12/1998 | Davila et al. |
| 5,897,588 A | 4/1999 | Hull et al. |
| 5,906,640 A | 5/1999 | Penn et al. |
| 5,913,895 A | 6/1999 | Burpee et al. |
| 5,913,897 A | 6/1999 | Corso, Jr. et al. |
| 5,922,020 A | 7/1999 | Klein et al. |
| 5,938,682 A | 8/1999 | Hojeibane et al. |
| 5,961,548 A | 10/1999 | Shmulewitz |
| 5,972,018 A | 10/1999 | Israel et al. |
| 6,013,091 A | 1/2000 | Ley et al. |
| 6,017,363 A | 1/2000 | Hojeibane |
| 6,036,682 A | 3/2000 | Lange et al. |
| 6,039,749 A | 3/2000 | Marin et al. |
| 6,048,361 A | 4/2000 | Von Oepen |
| 6,096,073 A | 8/2000 | Webster et al. ............ 623/1.16 |
| 6,099,497 A | 8/2000 | Adams et al. ........... 604/96.01 |
| 6,165,195 A * | 12/2000 | Wilson et al. .............. 606/194 |
| 6,217,527 B1 | 4/2001 | Selmon et al. |
| 6,221,080 B1 | 4/2001 | Power |
| 6,231,563 B1 | 5/2001 | White et al. |
| 6,436,134 B2 | 8/2002 | Richter et al. |
| 2002/0111675 A1 | 8/2002 | Wilson |

FOREIGN PATENT DOCUMENTS

| | | | |
|---|---|---|---|
| EP | 876805 | | 11/1998 |
| EP | 0897700 | | 2/1999 |
| EP | 0904745 | | 3/1999 |
| FR | 2678508 | | 7/1991 |
| WO | WO 88/06026 | | 2/1988 |
| WO | WO 92/19308 | | 11/1992 |
| WO | WO 96/41592 | | 6/1996 |
| WO | WO 97/33532 | | 3/1997 |
| WO | WO 97/45073 | | 5/1997 |
| WO | WO 97/26936 | * 7/1997 | .......... A61M/25/01 |
| WO | WO 98/17204 | | 4/1998 |
| WO | WO 98/35634 | | 8/1998 |
| WO | WO 98/36709 | | 8/1998 |
| WO | WO 98/44871 | | 10/1998 |
| WO | WO 98/48733 | | 11/1998 |
| WO | WO 98/52497 | | 11/1998 |
| WO | WO 99/15103 | | 4/1999 |
| WO | WO 99/17680 | | 4/1999 |
| WO | WO 99/39661 | | 8/1999 |
| WO | WO 99/65419 | | 12/1999 |
| WO | WO 00/00104 | | 1/2000 |
| WO | WO 00/12166 | | 3/2000 |
| WO | WO 00/13613 | | 3/2000 |

OTHER PUBLICATIONS

Carrie et al., "T–Shaped Stent Placement: A Technique for the Treatment of Dissected Bifurcation Lesions" *Catheterization and Cardiovascular Diagnosis*, (1996) 37:311–313.

Colombo et al., "Kissing stents for Bifurcational Coronary Lesion"*Catheterization and Cardiovascular Diagnosis*, (1993) 30:327–330.

Fischman et al., "A randomized Comparison of Coronary–Stent Placement and Balloon Angioplasty in the Treatment of Coronary Artery Disease" *The New England Journal of Medicine*, (1994) 331(8):496–501.

Katoh et al., "New Double Wire Technique to Stent Ostial Lesions" *Catheterization and Cardiovascular Diagnosis*, (1997) 40:400–402.

Lewis et al., "Acute Procedural Results in the Treatment of 30 Coronary Artery Bifurcation Lesions with a Double–Wire Atherectomy Technique for Side Branch Protection" *American Heart Journal*, (1994) 127:1600–1607.

Nakamura et al., "Techniques for Palmaz–Schatz Stent Deployment in Lesions With a Large Side Branch" *Catheterization & Cardiovascular Diagnosis*, (1995) 34:353–361.

SCIMED Life Systems, Inc.—TRIO™ 14 PTCA Catheter, *Re–engineering Over–the–Wire Balloon Technology*, Company Brochure, ©1994.

Serruys et al., "A Comparison of Balloon–Expandable–Stent Implantation with Balloon Angioplasty in Patients with Coronary Artery Disease" *The New England Journal of Medicine*, (1994) 331(8):489–495.

U.S. patent application Ser. No. 08/642,297, Filed May 3, 1996 to Richter et al.

* cited by examiner

FIG. 10

CATHETER WITH ATTACHED FLEXIBLE SIDE SHEATH

CROSS-REFERENCES TO RELATED APPLICATIONS

The present application is a continuation-in-part of pending U.S. patent application Ser. No. 09/325,996, filed on Jun. 4, 1999, now abandoned, which claims the benefit under 35 U.S.C. 119 of now expired U.S. Provisional Application No. 60/088,301, filed Jun. 5, 1998, and which is also a continuation-in-part of of expired PCT Application Number U599/00835, filed Jan. 13, 1999, which was published on Jul. 22, 1999 under Publication Number WO99/36002, and which is a continuation and claims priority of U.S. patent application Ser. No. 09/007,265, filed Jan. 14, 1998, which issued on Apr. 3, 2001 as U.S. Pat. No. 6,210,429 and which is a continuation-in-part of U.S. patent application Ser. No. 08/744,002 filed Nov. 4, 1996, now abandoned, all of which are incorporated herein by reference in their entireties.

TECHNICAL FIELD

The present invention relates to catheter systems for delivering stents.

BACKGROUND OF THE INVENTION

A type of endoprosthesis device, commonly referred to as a stent, may be placed or implanted within a vein, artery or other tubular body organ for treating occlusions, stenoses, or aneurysms of a vessel by reinforcing the wall of the vessel or by expanding the vessel. Stents have been used to treat dissections in blood vessel walls caused by balloon angioplasty of the coronary arteries as well as peripheral arteries and to improve angioplasty results by preventing elastic recoil and remodeling of the vessel wall. Two randomized multicenter trials have recently shown a lower restenosis rate in stent treated coronary arteries compared with balloon angioplasty alone (Serruys, P W et al., *New England Journal of Medicine* 331: 489–495 (1994) and Fischman, D L et al. *New England Journal of Medicine* 331:496–501 (1994)). Stents have been successfully implanted in the urinary tract, the bile duct, the esophagus and the tracheo-bronchial tree to reinforce those body organs, as well as implanted into the neurovascular, peripheral vascular, coronary, cardiac, and renal systems, among others. The term "stent" as used in this Application is a device which is intraluminally implanted within bodily vessels to reinforce collapsing, dissected, partially occluded, weakened, diseased or abnormally dilated or small segments of a vessel wall.

One of the drawbacks of conventional stents is that they are generally produced in a straight tubular configuration. The use of such stents to treat diseased vessels at or near a bifurcation (branch point) of a vessel may create a risk of compromising the degree of patency of the main vessel and/or its branches, or the bifurcation point and also limits the ability to insert a branch stent into the side branch if the result of treatment of the main, or main, vessel is suboptimal. Suboptimal results may occur as a result of several mechanisms, such as displacing diseased tissue, plaque shifting, vessel spasm, dissection with or without intimal flaps, thrombosis, and embolism.

As described in related copending U.S. patent application Ser. No. 08/744,022 filed Nov. 4, 1996, now abandoned; Ser. No. 09/007,265 filed Jan. 14, 1998; Ser. No. 08/935,383 filed Sep. 23, 1997; and 60/088,301 filed Jun. 5, 1998; and PCT Patent Application Publication No. WO 99/00835 filed Jan. 14, 1998; systems have been developed for deploying a main stent in a main vessel at the intersection of a main vessel and a branch vessel with a branch stent extending into a branch vessel through a side opening in the main stent. Unfortunately, several difficulties exist when attempting to position such an arrangement of a main and branch stents at a vessel intersection.

For example, the insertion of separate guidewires into both the main vessel and the secondary vessel is required before positioning a main stent in a main vessel with a branch stent projecting through a side opening in the main stent into a branch vessel. Main and branch stents are then advanced over the separate guidewires which have been pre-guided one after another into the respective main and branch vessels, such that the main stent can be deployed within the main vessel and the branch stent can be deployed through the side opening in the main stent into the branch vessel. Unfortunately, when attempting to guide two such separate guidewires through the main vessel such that one enters the branch vessel, the two guidewires typically tend to wrap around one another and become entangled. Additionally, time and effort is required to individually position each of the two guidewires one after another.

An additional disadvantage of conventional stents is the difficulty in visualizing the stents during and after deployment, and in general, the fact that they are not readily imaged by low-cost and easy methods, such as x-ray or ultrasound imaging.

SUMMARY OF THE INVENTION

The present invention provides a stent delivery system which comprises a catheter with a flexible side sheath attached thereto. In a preferred aspect of the invention, the catheter is adapted to receive a first guidewire therethrough, and the flexible side sheath is adapted to receive a second guidewire therethrough.

As will be explained, an advantage of the present stent delivery system is that it may be used for deploying a main stent in a main vessel with a side opening in the main stent being aligned with the ostium of a branch vessel. In additional preferred aspects, a branch stent can also be deployed in the branch vessel with the branch stent passing through the side opening in the main stent.

Accordingly, the present invention also sets forth methods of positioning a main stent at a vessel bifurcation such that a side opening in the main stent is positioned at the ostium of a branch vessel. In preferred aspects, a main guidewire is first positioned in the main vessel such that a distal end of the main guidewire extends past the bifurcation. Thereafter, the stent delivery system, (comprising a catheter with an attached flexible side sheath), is advanced to a position proximate the bifurcation, wherein the catheter is advanced over the main guidewire, and wherein the main stent is positioned over the catheter. In preferred aspects, the flexible side sheath is positioned to pass through the interior of the main stent, (positioned over the distal end of the catheter), and out of the side opening in the main stent.

Thereafter, a branch guidewire is advanced through the flexible side sheath and into the branch vessel. To assist in guiding the second guidewire into the branch vessel, the flexible side sheath may preferably taper to a narrow distal end, which may be curved slightly outwardly.

Subsequently, the stent delivery system is advanced with the catheter advancing over the main guidewire while the flexible side sheath concurrently advances over the branch guidewire. In one aspect of the invention, the side opening in the main stent is positioned in alignment with the ostium of the branch vessel due solely to the presence of the branch guidewire extending from an interior of the main stent out through the side opening in the main stent and into the branch vessel.

In another more preferred aspect of the invention, however, the side opening in the main stent is positioned in alignment with the ostium of the branch vessel by viewing relative movement of radiopaque markers positioned on each of the catheter and the flexible side sheath. In this aspect of the invention, the relative marker movement indicates that a portion of the flexible side sheath which is positioned adjacent the side opening in the main stent is advancing into the ostium of the branch vessel, thereby indicating the position of the side opening of the main stent with respect to the ostium of the branch vessel. In this aspect of the invention, the flexible side sheath will deflect into the branch vessel as it is advanced over the second guidewire, (while the catheter itself moves distally along through the main vessel over the first guidewire).

Such relative movement of the radiopaque markers may be viewed as a rotation of a marker on the flexible side sheath with respect to a marker(s) on the catheter, or as a separation between the marker on the flexible side sheath with respect to a marker(s) on the catheter. In certain aspects, the marker on the flexible side sheath is positioned adjacent a marker on the catheter, such that the relative marker motion will be viewable in an image as a separation occurring between the two markers. In a preferred aspect of the invention, the relative movement of the markers on the catheter and flexible side sheath can be observed fluoroscopically as the markers are radiopaque and are preferably made of suitable materials including tungsten and gold.

In addition, a plurality of markers may be positioned on the catheter with a marker positioned at locations corresponding to each of the proximal and distal ends of the main stent. A medial marker may also be included, positioned halfway between the distal and proximal markers, for indicating the position of the side hole in the main stent, (which is preferably positioned halfway between the distal and proximal ends of the stent).

In additional aspects of the present invention, the main stent is deployed in the main vessel, (such as by an inflatable balloon at the distal end of the catheter). Thereafter, a branch stent may be advanced through the at least partially deployed main stent and positioned in the branch vessel. Preferably, the branch stent is advanced through the at least partially deployed main stent by a second catheter, which then deploys the branch stent in the branch vessel, (such as by an inflatable balloon at the distal end of the second catheter).

To deploy the branch stent, the delivery system, (comprising the catheter and attached flexible side sheath), may be removed leaving the two guidewires in place such that the second catheter can then be advanced over the second guidewire and into the branch vessel. As such, the second catheter can then be advanced over the second guide wire with its distal end extending into the branch vessel.

An advantage of the present stent delivery system is that it avoids having to separately position first and second guidewires within the respective main and branch vessels prior to deployment of the main and branch stents thereover. Rather, with the present invention, only a single guidewire needs to initially be placed within the main vessel, with the delivery system subsequently deploying both the main and branch stents thereover.

The main stent may optionally include outwardly expandable portions which can be expanded from an initial position which is flush with the cylindrical body of the stent to protrude outwardly from the side opening in the main stent, thereby anchoring into the walls of the branch vessel, holding the side opening in registry with the ostium of the branch vessel. In an exemplary aspect, the cylindrical body of the main stent has an even surface, with an expandable portion positioned within the side opening of the cylindrical body, such that it is flush with the cylindrical body prior to expansion.

In addition, the branch stent may optionally comprise a contacting portion at its proximal end to secure the proximal end of the branch stent to the side opening in the main stent. In an exemplary aspect, the contacting portion comprises a flared proximal end.

Applications of the present system include the cardiac, coronary, renal, peripheral vascular, gastrointestinal, pulmonary, urinary and neurovascular systems and the brain. Further advantages of the present stent delivery system are that it provides an improved stent delivery apparatus, which may deliver main and branch stents to: 1) completely cover the bifurcation point of bifurcation vessels; 2) be used to treat lesions in one branch of a bifurcation while preserving access to the other branch for future treatment; 3) allow for differential sizing of the stents in a bifurcated stent apparatus even after a main stent is implanted; 4) treat bifurcation lesions in a bifurcated vessel where the branch vessel extends from the side of the main vessel; and 5) be marked with, or at least partly constructed of, material which is imageable by commonly used intraluminal catheterization visualization techniques including but not limited to ultrasound or x-ray.

DESCRIPTION OF THE SPECIFIC EMBODIMENTS

The present invention comprises methods of positioning a main stent at a vessel bifurcation such that a side opening in the main stent is positioned at the ostium of a branch vessel, and sets forth various apparati and kits for performing the preferred methods.

In addition, the present invention comprises methods for positioning a main and a branch stent at a vessel bifurcation, wherein the branch stent is deployed through a side opening in the main stent, with the side opening in the main stent being positioned in registry with the ostium of the branch vessel.

Figure 1:
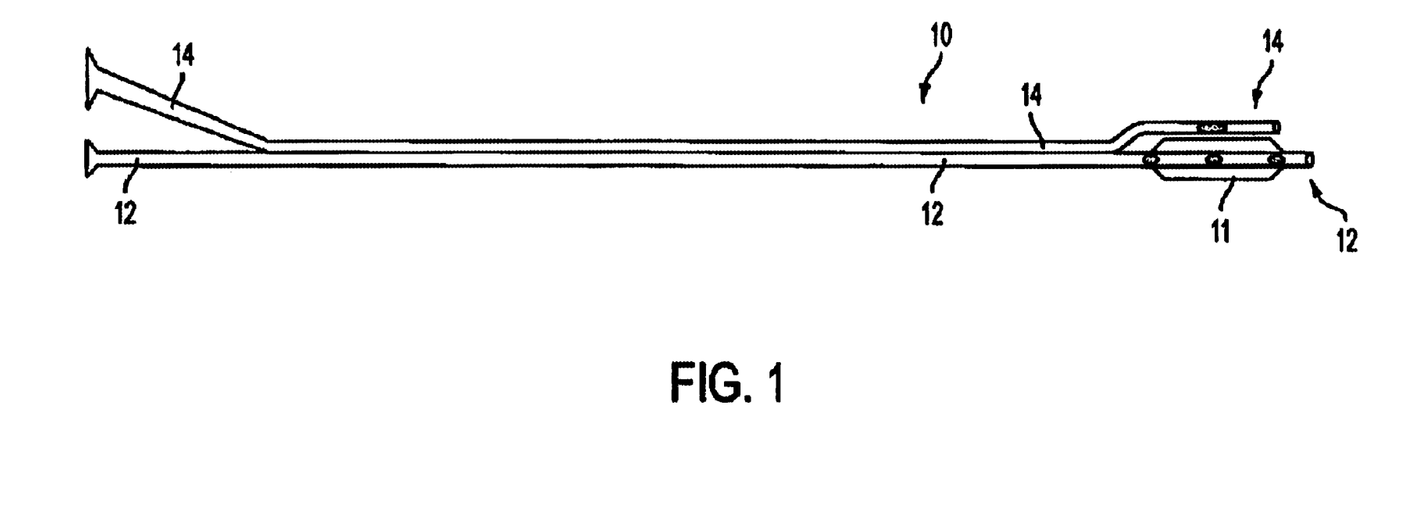
FIG. 1 is an illustration of the present stent delivery system, showing a catheter with a flexible side sheath attached thereto.
Figure 2A:
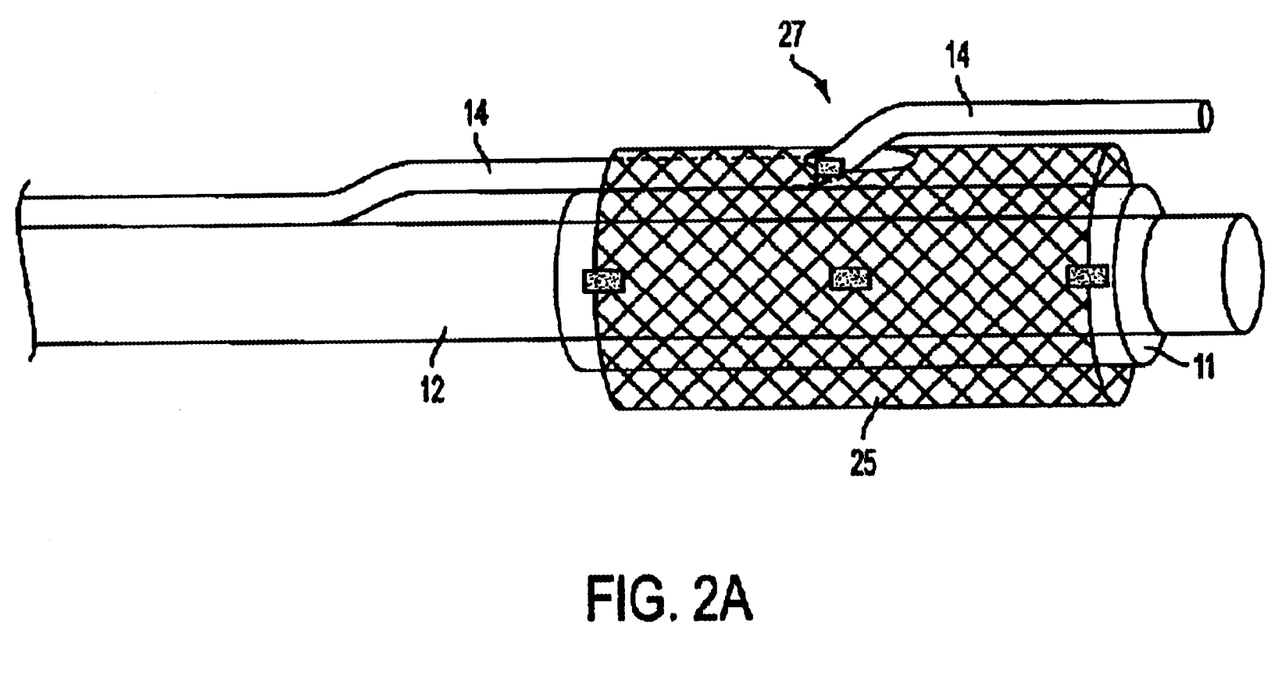
FIG. 2A is a close up illustration of the distal end of the stent delivery system of FIG. 1 with a main stent positioned thereon.
Figure 2B:
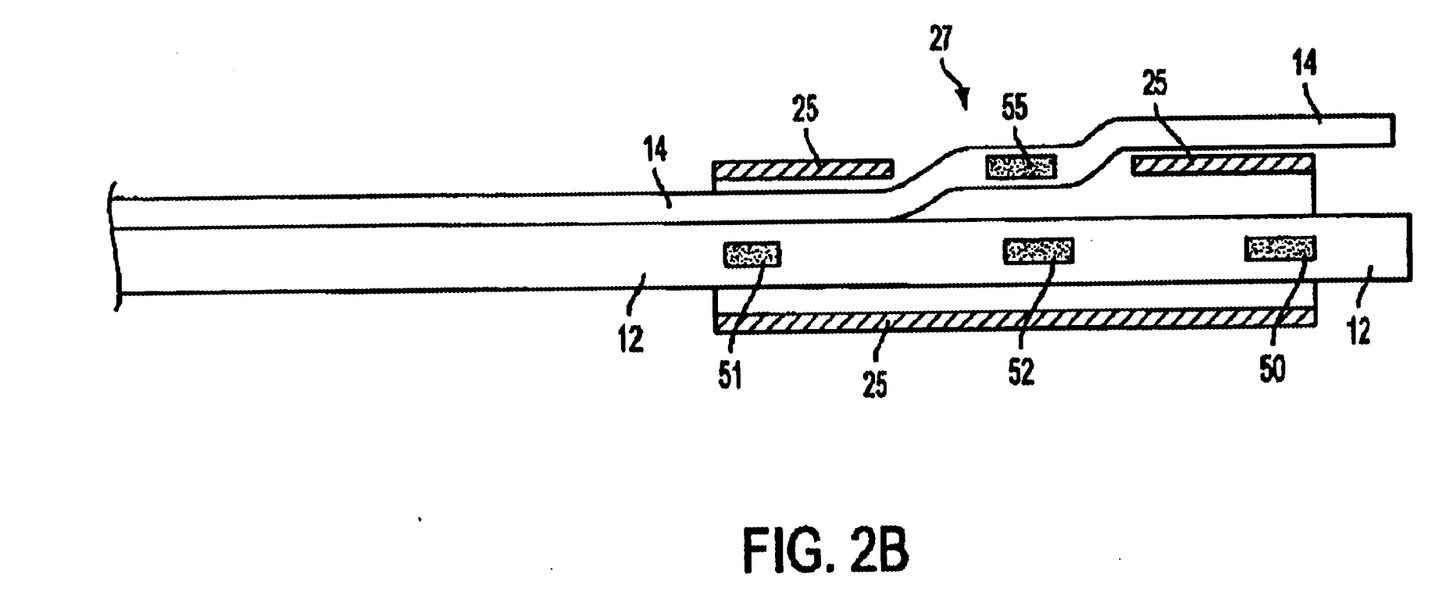
FIG. 2B is a sectional side elevation view corresponding FIG. 2A.
Figure 5:
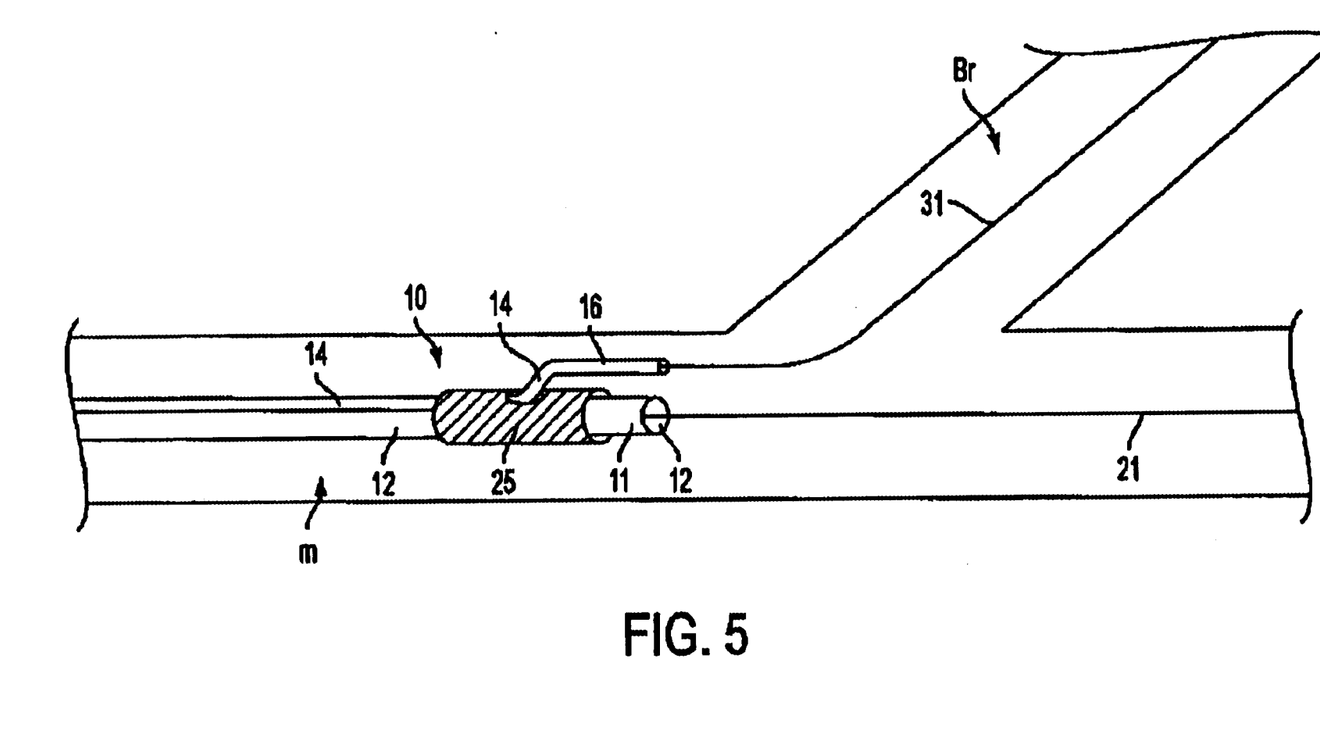
FIG. 5 is an illustration of the second guidewire being advanced out of the distal end of the side sheath, through a side opening in a main stent and into the branch vessel.
Figure 6A:
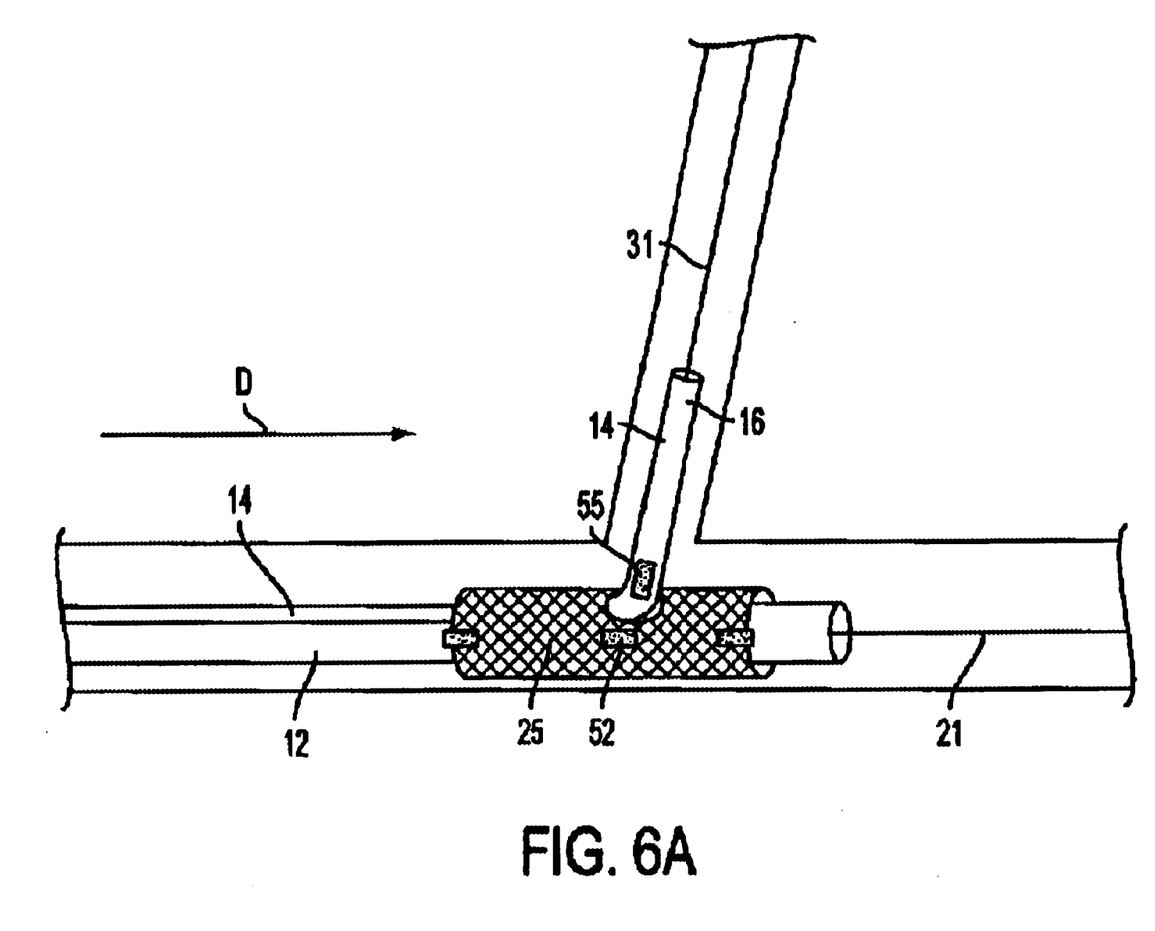
FIG. 6A is an illustration of the catheter and attached flexible side sheath advanced over the first and second guidewire such that the distal end of the flexible side sheath is deflected into the branch vessel, showing the separation between radiopaque markers on the catheter and flexible side sheath.
Figure 6B:
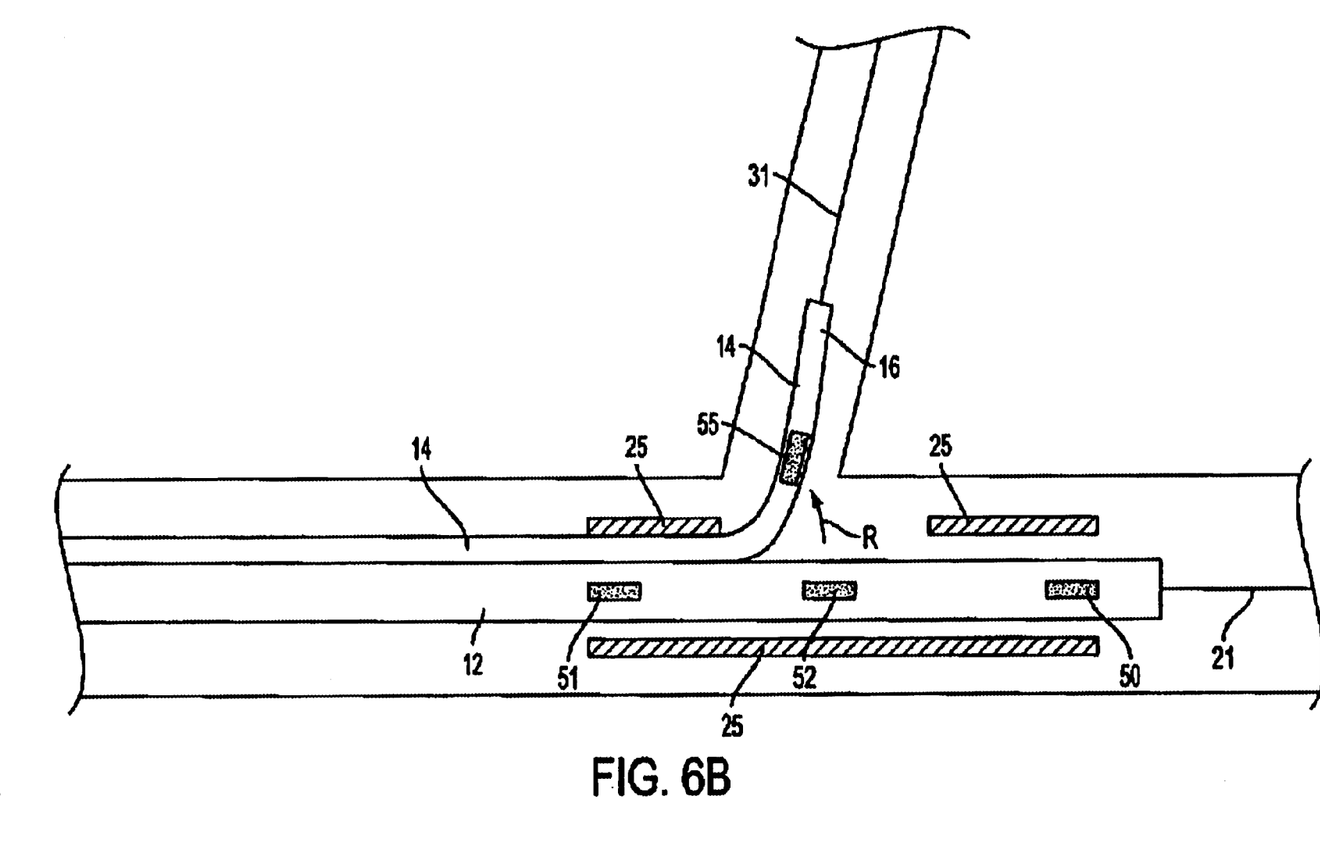
FIG. 6B is a sectional side elevation view corresponding FIG. 6A.

A novel stent delivery system is provided for accomplishing the preferred methods. Referring to FIGS. 1 to 2B, the present stent delivery system 10 comprises a first catheter 12 having an attached flexible side sheath 14. An inflatable balloon 11 is preferably positioned at the distal end of first catheter 12. As is shown in FIGS. 5 to 6B, first catheter 12 is receivable over a first guidewire 21 and flexible side sheath 14 is receivable over a second guidewire 31. As can be seen, stent 25 is preferably crimped down onto flexible side sheath 14, as shown. Preferably, stent 25 is initially crimped onto balloon 11 with distal end 16 of side sheath 14 projecting outwardly through side opening 27 as shown.

The present invention provides a method of positioning a main stent 25 at a vessel bifurcation B such that a side opening 27 in main stent 25 is positioned at the ostium of a branch vessel Br, as follows.

Figure 3:
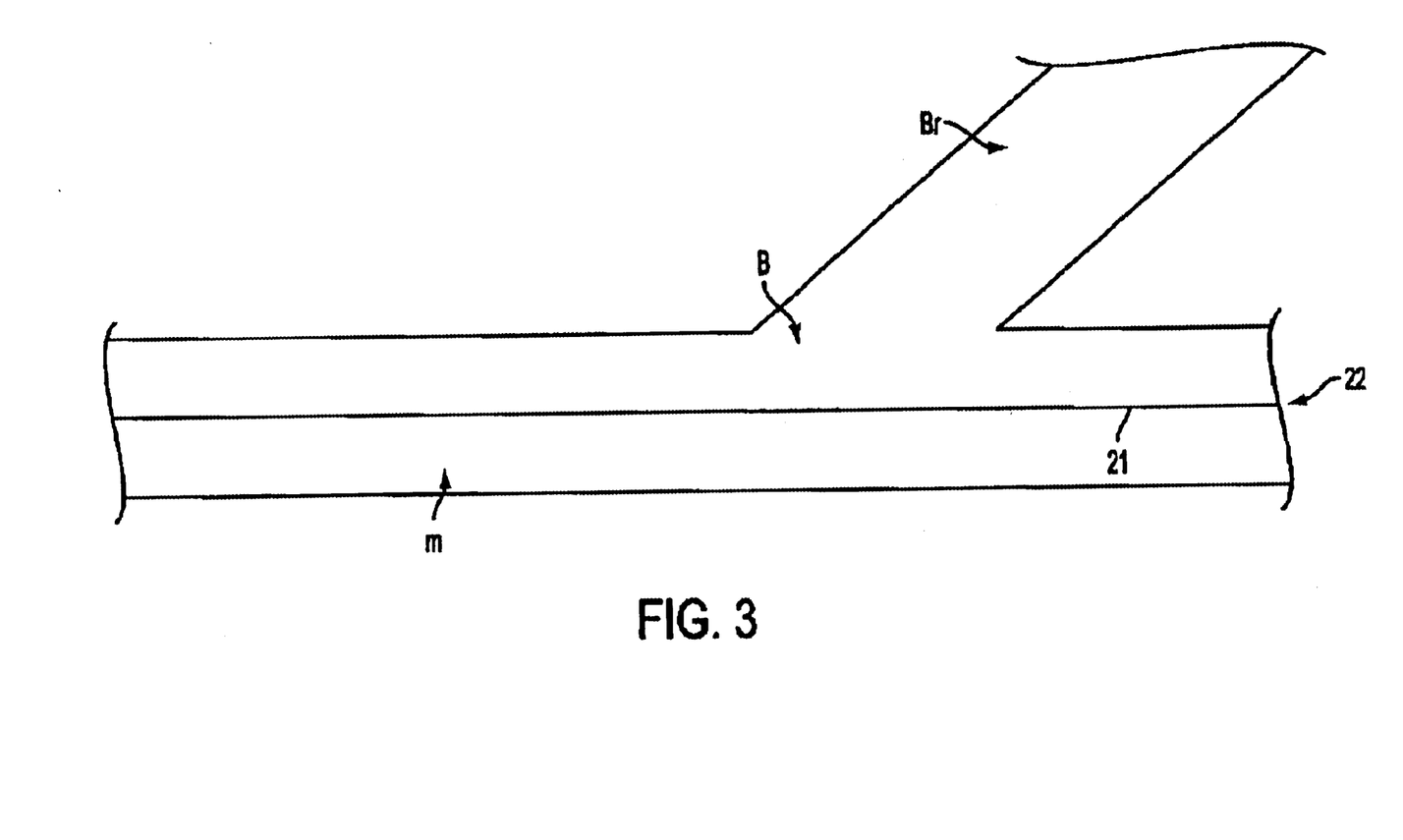
FIG. 3 is an illustration of a placement of first guidewire within a main vessel.
Figure 4:
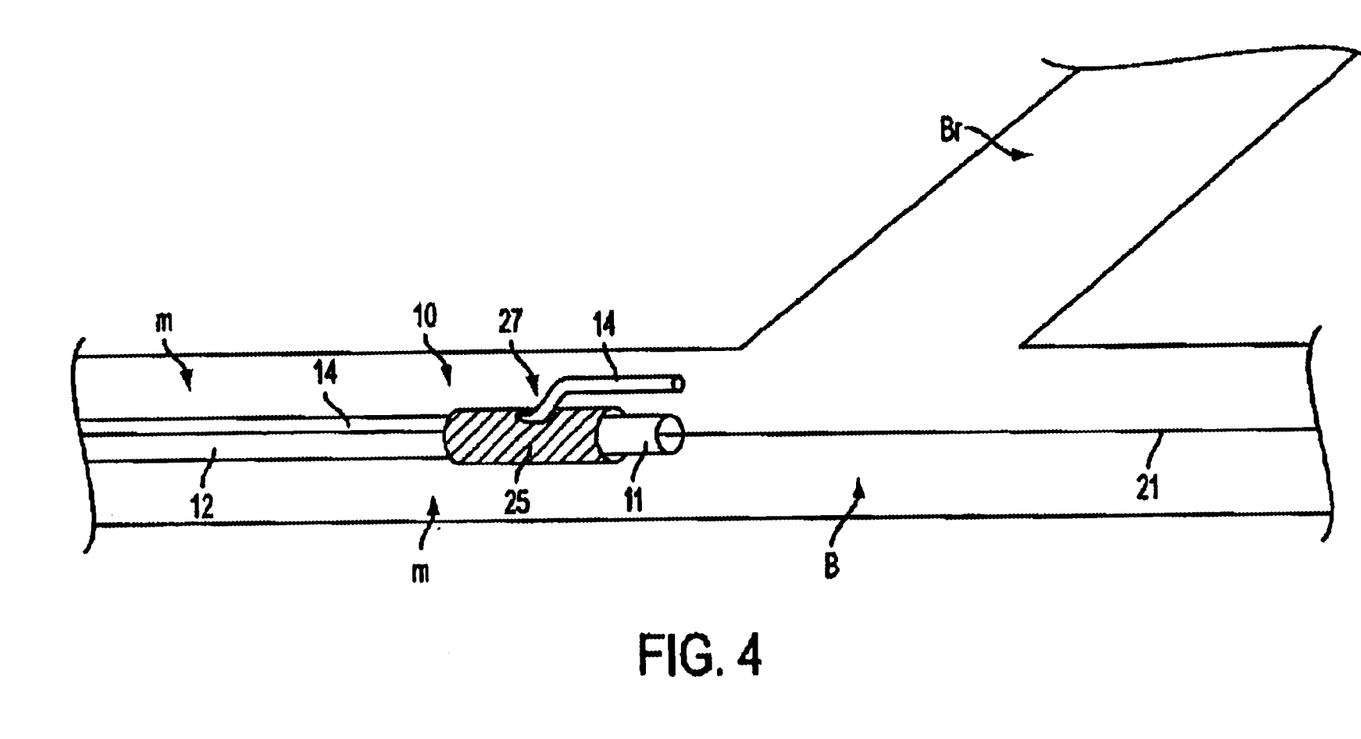
FIG. 4 is an illustration of the catheter and attached flexible side sheath of the present invention advanced over the first guidewire to a position near the ostium of the branch vessel.

Referring to FIG. 3, a main guidewire 21 is first positioned in the main vessel M such that a distal end 22 of main guidewire 21 extends past bifurcation B. Referring to FIG. 4, stent delivery system 10 is then advanced to a position proximate bifurcation B, wherein catheter 12 is received over first guidewire 21, and wherein main stent 25 is positioned over catheter 12 with flexible side sheath 14 positioned to pass through the interior of main stent 25 and out of side opening 27 in main stent 25, as shown. Referring to FIG. 5, second guidewire 31 is then advanced through flexible side sheath 14 attached to catheter 12 and into branch vessel Br.

In one aspect of the invention, side opening 27 in main stent 25 is positioned in alignment with the ostium of branch vessel Br simply by the presence of second guidewire 31 extending from an interior of main stent 25 out through side opening 27 in main stent 25 and into branch vessel Br. In this aspect of the invention, the insertion of a branch stent over guidewire 31 through side opening 27 in main stent 25 and into branch vessel Br serves to align the side opening 27 with the ostium of branch vessel Br.

In another more preferred aspect, however, stent delivery system 10, (comprising catheter 12 and attached flexible side sheath 14), are subsequently advanced distally in direction D to the position as shown in FIGS. 6A and 6B, with catheter 12 being advanced over first guidewire 21 while flexible side sheath 14 is advanced over second guidewire 31. In this aspect of the invention, an operator views relative movement between a radiopaque marker positioned on the flexible side sheath with respect to at least one radiopaque marker positioned on the catheter, wherein the relative marker movement indicates that a portion of the flexible side sheath adjacent the side opening in the main stent is advancing into the ostium of the branch vessel, thereby indicating the position of the side opening of the main stent with respect to the ostium of the branch vessel.

Specifically, referring to FIGS. 2B and 6B, a distal marker 50, a proximal marker 51 and a medial marker 52 may be disposed on catheter 12. Preferably, the location of proximal marker 51 corresponds to the location of the proximal end of stent 25, the location of distal marker 50 corresponds to the location of the distal end of stent 25, and the location of medial marker 52 corresponds to the location of side opening 27 of stent 25. At least one marker 55 is positioned on flexible side sheath 14 as shown. Preferably, marker 55 is positioned adjacent to medial marker 52.

As can be seen by comparing FIGS. 2B to 6B, as stent delivery system 10 is advanced distally such that the distal end of flexible side sheath 14 is received in branch vessel Br, (FIG. 6B), marker 55 will move in direction R relative to markers 50, 51 and 52. In particular, an increasing separation distance will occur between marker 55 positioned on flexible side sheath 14 and marker 52 positioned on catheter 12 as catheter 12 is advanced distally over first guidewire 21 while flexible side sheath 14 is simultaneously advanced distally over second guidewire 31.

In an additional aspect of the invention, each of marker 52 and 55 are slightly elongated and rectangle shaped, (as shown), such that relative rotational movement therebetween can also be observed. Marker 55 may be made of tungsten and markers 50, 51 and 52 may be made of gold.

When the operator views the relative motion between markers 52 and 55, this indicates that the portion of flexible side sheath 14 positioned adjacent side opening 27 is disposed at the ostium of branch vessel Br. By viewing the position of markers 50, 51 and 52, the operator can also determine the position of the distal and proximal ends of stent 25 and the position of side opening 27 with respect to the ostium of branch vessel Br.

The present invention also comprises systems for deploying a branch stent into branch vessel Br with main stent 25 positioned such that side opening 27 is in registry with the ostium of branch vessel Br. In these aspects of the invention, as illustrated in FIGS. 7 through 10, branch stent 40 is advanced through the interior of main stent 25, passing through side opening 27 and into branch vessel Br.

Figure 7A:
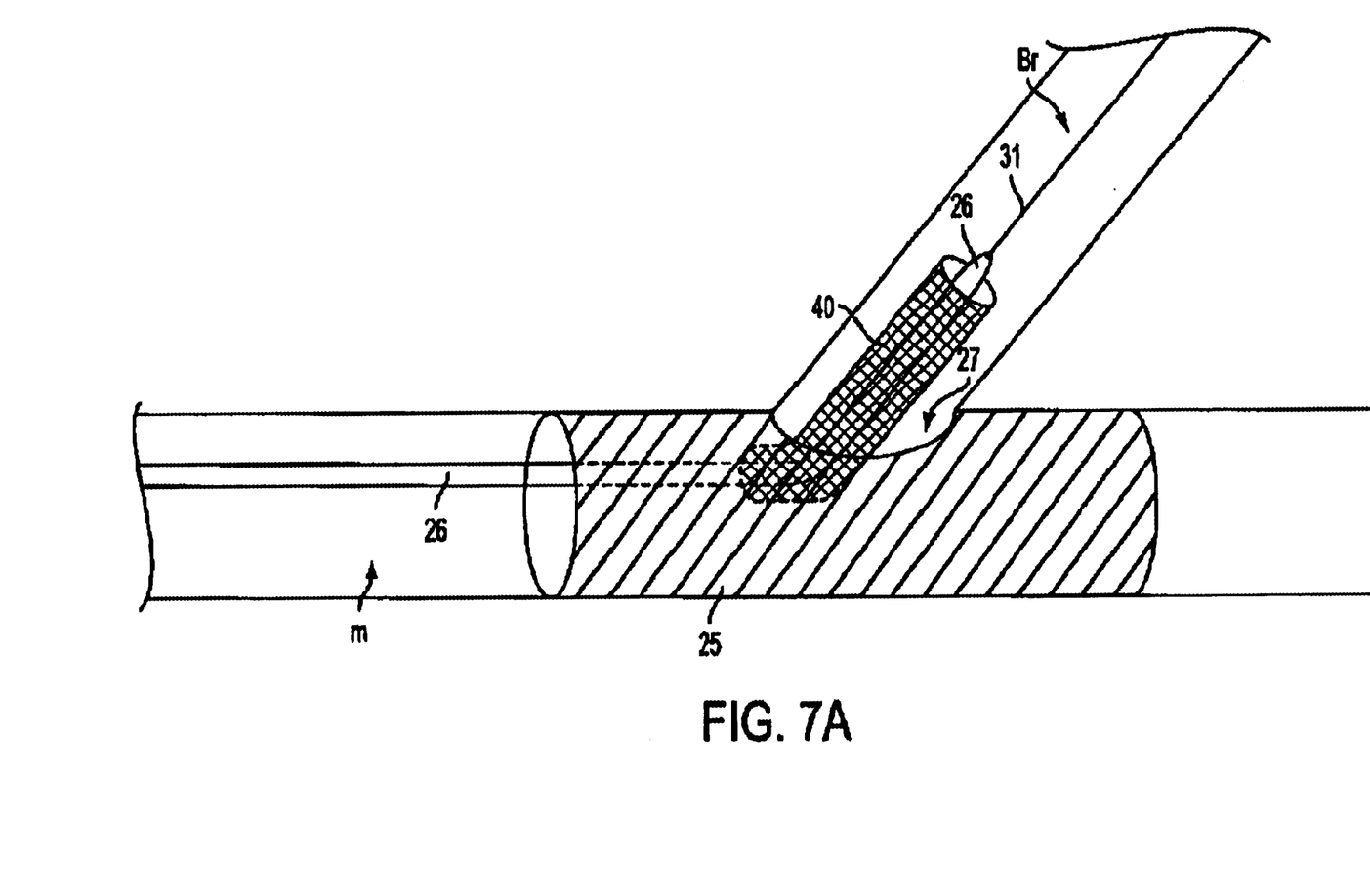
FIGS. 7A and 7B is an illustration of a branch stent advanced over the second guidewire and through the side opening in the main stent and into the branch vessel.

FIG. 7A is an illustration of branch stent 40, (disposed on the distal end of a second catheter 26), being advanced over second guidewire 31, passing through side opening 27 in main stent 25 into branch vessel Br. As can be seen, in one aspect of the present invention, stent delivery system 10 may first fully deploy main stent 25 and then be removed. Thereafter, second catheter 26 can be advanced over second guidewire 31 to position stent 40 for deployment in the branch vessel.

Figure 7B:
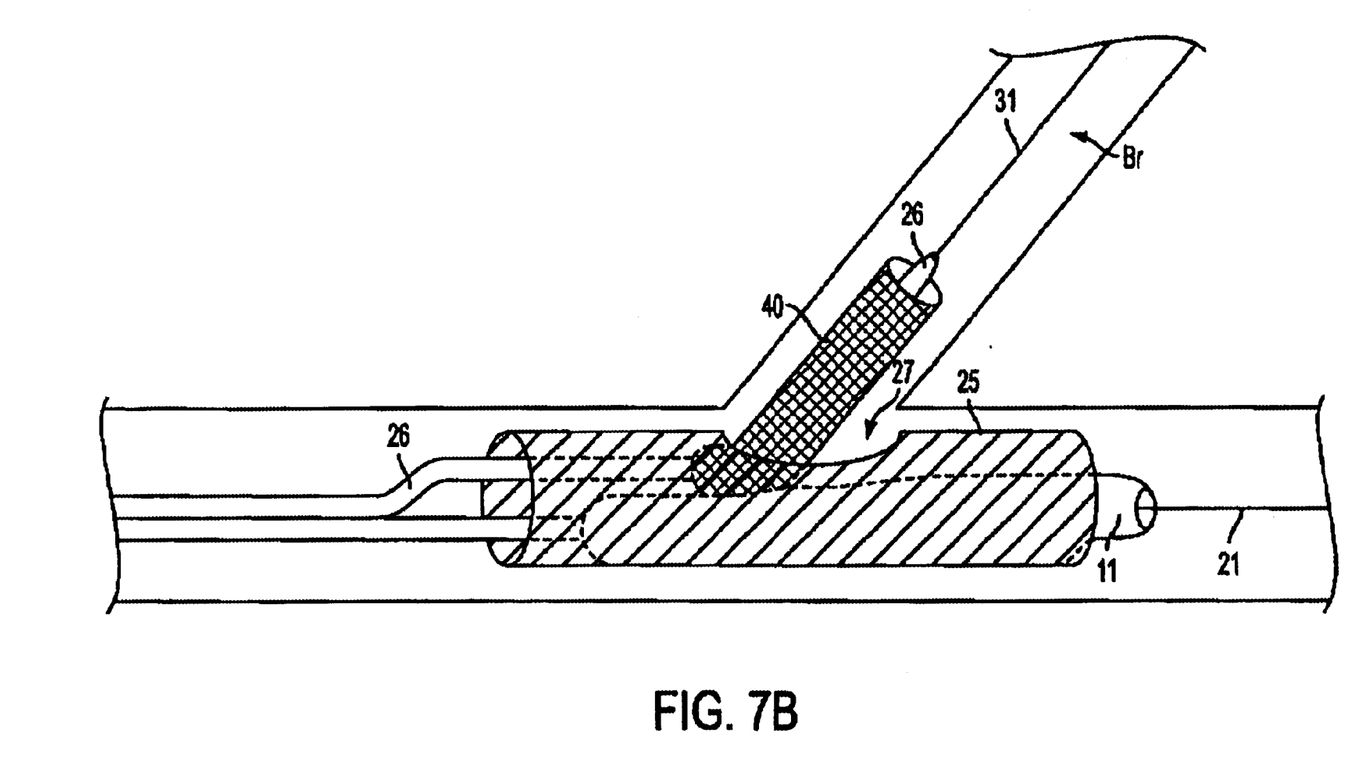

In an alternative aspect of the invention, as shown in FIG. 7B, stent 25 may be partially deployed in main vessel M and second catheter 26 may then be advanced through the partially expanded interior of main stent 25, passing out through side opening 27 in main stent 25 while stent delivery system 10 remains adjacent bifurcation B.

Figure 8:
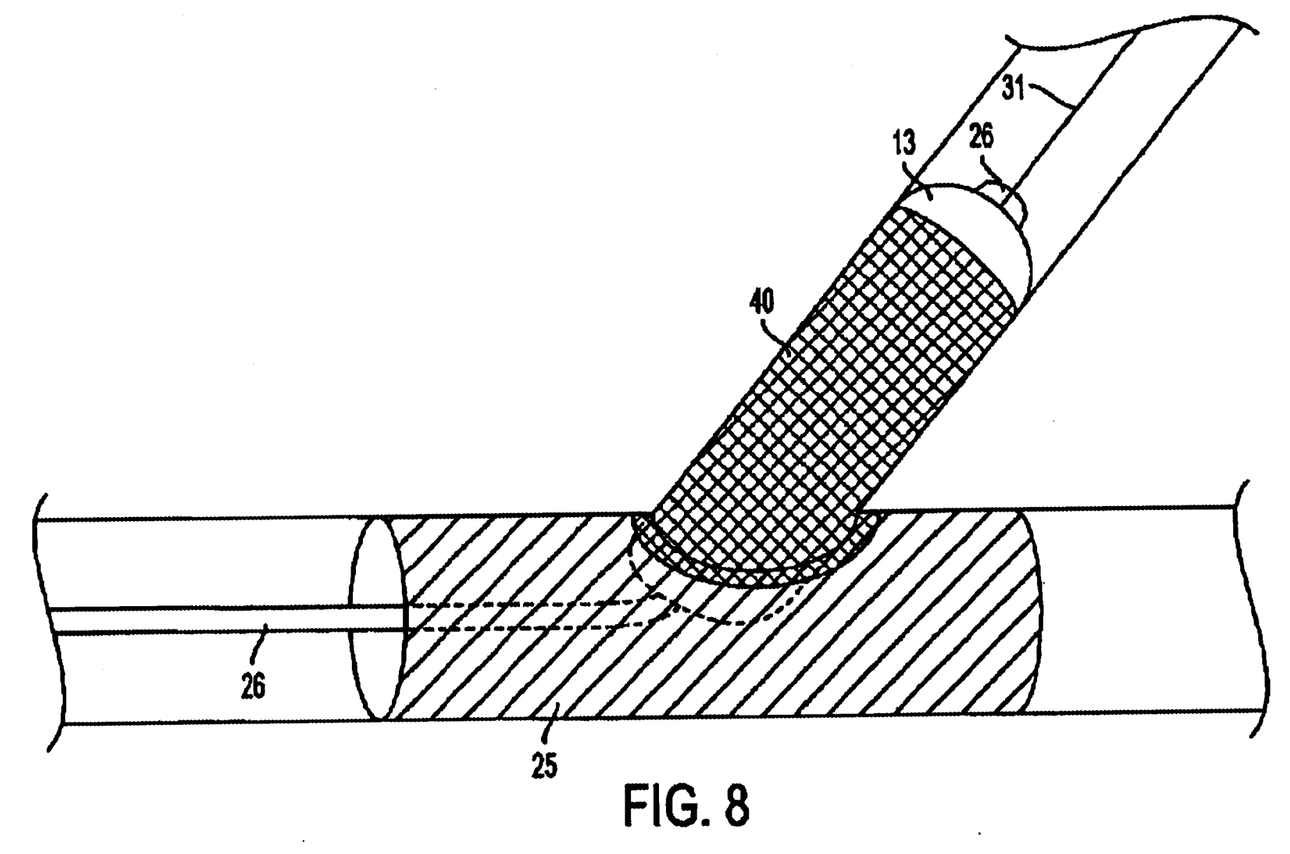
FIG. 8 is an illustration of the deployment of the branch stent by a balloon disposed on a second catheter received over the second guidewire.

FIG. 8 is an illustration of the deployment of branch stent 40 by a balloon 13 disposed on the distal end of second catheter 26, which is itself received over second guidewire 31. In this aspect of the invention an inflatable balloon 13 disposed at the distal end of second catheter 26 is used to deploy branch stent 40.

Figure 9:
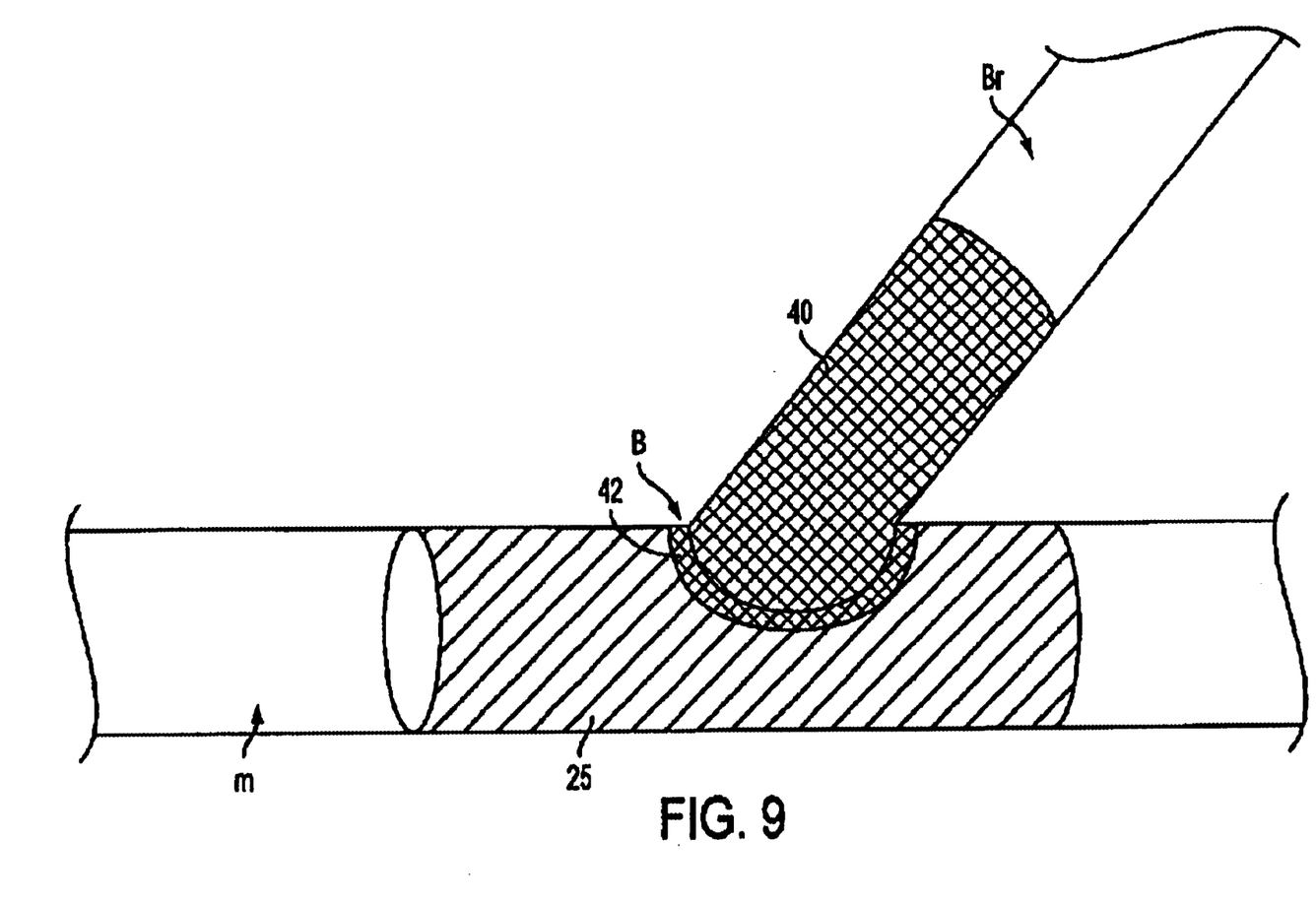
FIG. 9 is an illustration of the fully deployed main and branch stents with the guidewires and stent delivery system removed.

FIG. 9 is an illustration of the fully deployed main and branch stents 25 and 40 with the guidewires (21 and 31) and stent delivery system (10) removed. As can also be seen, stent 40 may further comprise a contact portion 42 which remains disposed within side opening 27 thereby securing the proximal end of stent 40 to side opening 27 of stent 25, thereby providing a bifurcated stent arrangement covering vessel bifurcation B. Such a contacting portion 42 is further described in copending PCT Patent Application WO 99/00835, filed Jan. 14, 1998.

Figure 10:
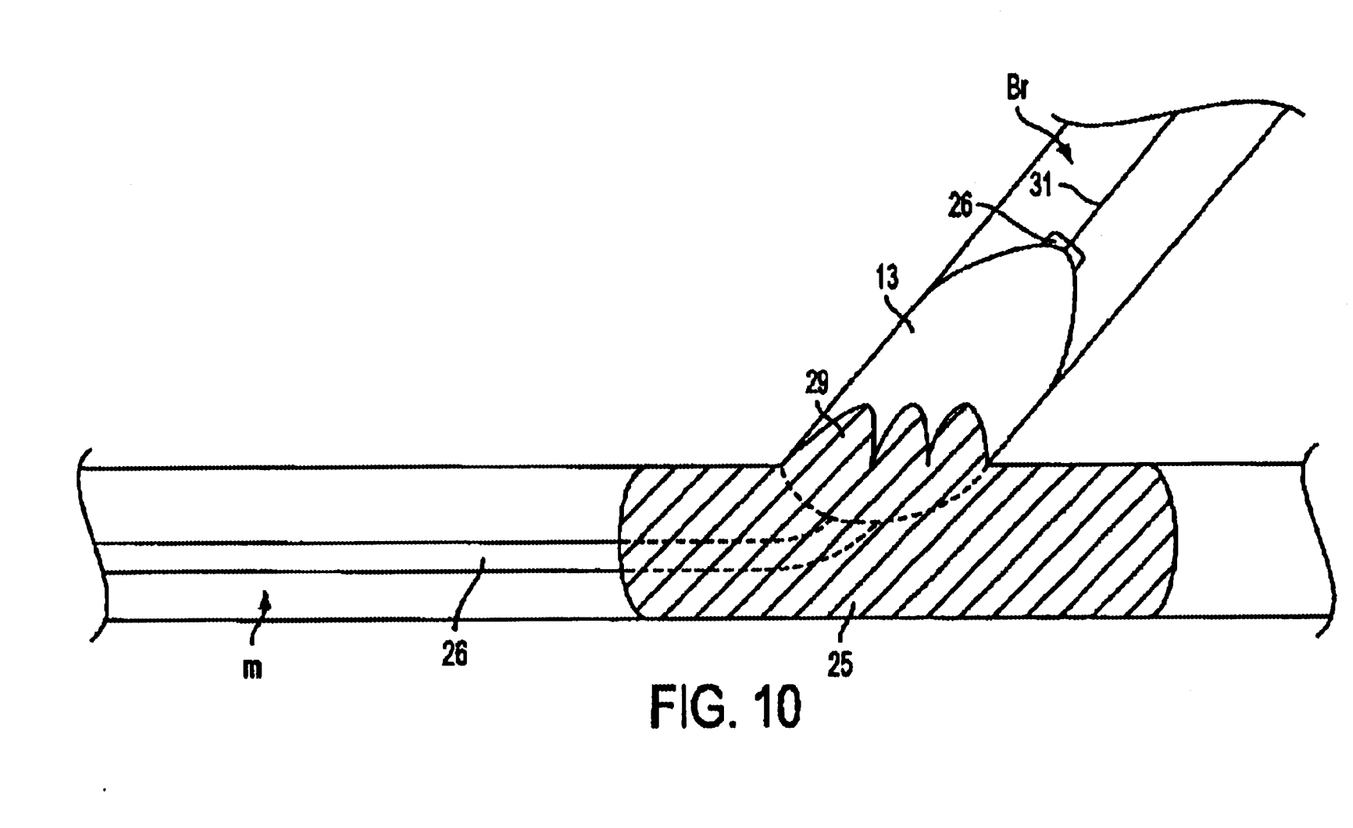
FIG. 10 shows an embodiment of the present invention with outwardly expandable portions disposed around the side opening on the main stent.

Lastly, FIG. 10 shows an embodiment of the present invention with outwardly expandable portions disposed around the side opening on the main stent. Specifically, balloon 13 on catheter 26 can also be inflated to deploy radially expandable portions 29 which extend laterally outward from an initial position flush with the cylindrical body of stent 25 to a position where portions 29, (disposed around the edges of side opening 27), are anchored against the walls of branch vessel B, such that side opening 27 is positioned in registry with the ostium of branch vessel B. Further description of such radially expandable portions 29 which extend laterally outward from the edges of side opening 27 is set forth in Published PCT Patent Application No. WO 99/00835 filed Jan. 14, 1998, incorporated herein by reference in its entirety.

The present invention also comprises kits including the apparatus of the present invention with instructions for use setting forth any of the herein disclosed methods for use.

What is claimed is:

1. A delivery system for positioning at a vessel bifurcation, the system comprising:
    a catheter having a catheter marker positioned thereon; and
    a flexible side sheath positioned alongside said catheter, the flexible side sheath having a side sheath marker positioned thereon, wherein said catheter marker and said side sheath marker are aligned such that upon positioning of the flexible side sheath at the ostium, said flexible side sheath is positioned and configured to enter the branch vessel, thereby separating said catheter marker and said side sheath marker.

2. The delivery system of claim 1, further comprising a stent, wherein the catheter is positioned through the stent.

3. The delivery system of claim 2, wherein said side sheath is attached to said catheter at a first end of said side sheath and is positioned through a side opening of the stent at a second end of said side sheath.

4. The delivery system of claim 2, wherein said stent has a side opening configured to be positioned at an ostium of a branch vessel and the flexible side sheath is positioned through the stent such that a distal end of the flexible side sheath projects through said side opening.

5. The delivery system of claim 1, wherein said catheter marker comprises a distal and a proximal marker.

6. The delivery system of claim 3, wherein said catheter marker comprises a middle marker positioned between said distal and proximal markers.

7. The delivery system of claim 4, wherein said side sheath marker is adjacent to said middle marker.

8. The delivery system of claim 1, further comprising a balloon positioned at a distal end of the catheter.

9. The delivery system of claim 1, wherein said catheter marker is radiopaque.

10. The delivery of claim 9 wherein said catheter marker is comprised of gold.

11. The delivery system of claim 9, wherein said catheter marker is comprised of tungsten.

12. The delivery system of claim 1, wherein said side sheath marker is radiopaque.

13. The delivery system of claim 12, wherein said side sheath marker is comprised of tungsten.

14. The delivery system of claim 12, wherein said side sheath marker is comprised of gold.

15. The delivery system of claim 1, further comprising: a first guidewire receivable through said catheter; and
    a second guidewire receivable through said flexible side sheath.

16. A delivery system for positioning at an ostium of a branch vessel, the system comprising:
    a catheter comprising a proximal marker; a middle marker; and a distal marker; and
    a flexible side sheath positioned alongside said catheter, said side sheath having a side sheath marker,
    wherein said side sheath marker is aligned with said middle marker.

17. The delivery system of claim 16, wherein a first configuration, said side sheath marker is indistinguishable from said middle marker by a visualization method and wherein in a second configuration, said side sheath marker is distinguishable from said middle marker by said visualization method.

18. The delivery system of claim 17, wherein said visualization method is fluoroscopy.

19. The delivery system of claim 16, further comprising a stent with a side opening, and wherein said middle marker is located at the side opening of the stent.

20. The stent delivery system of claim 19, wherein said proximal and distal markers are located at two edges of the stent.

21. A stent delivery system for positioning a stent with a side branch access opening at an ostium of a branch vessel, the system comprising:
    a catheter having a catheter marker;
    a side sheath positioned alongside said catheter, said side sheath having a side sheath marker; and
    a stent with a branch access opening, wherein said catheter is positioned through said stent and said side sheath passes through said stent with a distal end of said side sheath projecting through said branch access opening of said stent, said catheter marker and said side sheath marker are aligned prior to positioning of the branch access opening of the stent at the ostium, and said catheter marker and said side sheath marker are separated when the side sheath is configured to enter the branch vessel and the branch access opening of the stent is substantially aligned with the ostium of the branch vessel.

22. The stent delivery system of claim 21, wherein said catheter marker comprises a distal and a proximal marker.

23. The stent delivery system of claim 22, wherein said catheter marker includes a middle marker positioned between said distal and proximal markers.

24. The stent delivery system of claim 23, wherein said side sheath marker is adjacent to said middle marker.

* * * * *